United States Patent
Shibuya et al.

(10) Patent No.: US 6,953,859 B2
(45) Date of Patent: Oct. 11, 2005

(54) PRODUCTION PROCESS FOR 5-ALKYL-OXAZOLIDIN-2,4-DIONE

(75) Inventors: Akira Shibuya, Kawasaki (JP); Yoshio Fujiwara, Kawasaki (JP); Yoshiaki Miyota, Kawasaki (JP); Norihito Nishimura, Kawasaki (JP); Makoto Saito, Kawasaki (JP)

(73) Assignee: Showa Denko K.K., Tokyo (JP)

( * ) Notice: Subject to any disclaimer, the term of this patent is extended or adjusted under 35 U.S.C. 154(b) by 80 days.

(21) Appl. No.: 10/343,607

(22) PCT Filed: Jun. 4, 2002

(86) PCT No.: PCT/JP02/05480

§ 371 (c)(1),
(2), (4) Date: Feb. 3, 2003

(87) PCT Pub. No.: WO02/098867

PCT Pub. Date: Dec. 12, 2002

(65) Prior Publication Data

US 2003/0181729 A1 Sep. 25, 2003

Related U.S. Application Data

(60) Provisional application No. 60/297,787, filed on Jun. 14, 2001.

(30) Foreign Application Priority Data

Jun. 5, 2001  (JP) ........................................ 2001-170044
Jun. 11, 2001 (JP) ........................................ 2001-175713

(51) Int. Cl.[7] .......................................... C07D 263/44
(52) U.S. Cl. ...................................................... 548/226
(58) Field of Search ......................................... 548/226

(56) References Cited

U.S. PATENT DOCUMENTS 2,338,220 A * 1/1944 Wallingford ................ 548/226
2,866,734 A * 12/1958 Shapiro et al. .............. 514/340
4,220,787 A * 9/1980 Scholz ........................ 548/226
4,812,471 A * 3/1989 Schnur ........................ 514/372
6,057,351 A * 5/2000 Galey et al. ................ 514/376

FOREIGN PATENT DOCUMENTS

| GB | 829 048 | | 2/1960 |
| GB | 829048 | * | 2/1960 |
| JP | 9-048769 A | | 2/1997 |
| JP | 11-171876 A | | 6/1999 |
| WO | WO 02 14292 | | 2/2002 |

OTHER PUBLICATIONS

Clark–Lewis J W: "2, 4 Oxazolidinediones." Chemical Reviews, American Chemical Society, Easton, US, vol. 58, 1958, pp. 63–99.
Wallingford et al.: "Alkyl Carbonates in Synthetic Chemistry. VI. Condensation with Alpha–Hydroxy Amides. A New Method for Preparing 2, 4–Oxazolidinediones." J. Am. Chem. Soc., vol. 67, 1945, p. 522–523.
Patent Abstracts of Japan, JP 11–171876 dated Jun. 29, 1999, Konica Corp.
Patent Abstracts of Japan, JP 9–048769 dated Feb. 18, 1997, Mitsubishi Gas Chem. Co. Inc.
V. H. Wallingford et al., "Alkyl Carbonates in Synthetic Chemistry, VI. Condensation with α–Hydroxy Amides. A New Method for Preparing 2, 4–Oxazolidinediones", J. Am. Chem. Soc., 67, 1945, p. 522.

* cited by examiner

Primary Examiner—Fiona T. Powers
(74) Attorney, Agent, or Firm—Sughrue Mion, PLLC

(57) ABSTRACT

The object of the present invention is to produce a 5-alkyl-oxazolidin-2,4-dione by an industrially advantageous method. The invention relates to novel process for producing a high-purity 5-alkyl-oxazolidin-2,4-dione comprising the steps of reacting a 2-hydroxycarboxylic acid amide with a carbonic acid ester in the presence of a metal alcoholate, thereby completing the reaction in one step, and then isolating the reaction product by a neutralization crystallization method.

28 Claims, No Drawings

PRODUCTION PROCESS FOR 5-ALKYL-OXAZOLIDIN-2,4-DIONE

CROSS REFERENCES OF RELATED APPLICATIONS

This application is an application filed under 35 U.S.C. §111(a) claiming benefit pursuant to 35 U.S.C. §119(e) (1) of the filing date of provisional Application No. 60/297,787 filed on Jun. 14, 2001, pursuant to 35 U.S.C. §111(b).

TECHNICAL FIELD

The present invention relates to a production process of a 5-alkyl-oxazolidin-2,4-dione which is useful as a raw material for syntheses of medical or agrochemical preparations or as a raw material of photographic chemicals.

BACKGROUND ART

As for the production method of oxazolidin-2,4-dione derivatives, a method of synthesizing the derivative by the reaction of a corresponding ester or amide form with urea is known and this method is already practiced in industry for a part of such derivatives (see, J. Am. Chem. Soc., 67, 522 (1945), and JP-A-09-48769 (the term "JP-A" as used herein means an "unexamined published Japanese patent application")).

However, as for the production method particularly of 5-alkyl-oxazolidin-2,4-dione represented by formula (2) of the present invention, only JP-A-11-171876 is known.

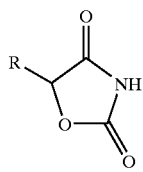

(2)

(wherein R represents an ethyl group, a propyl group or a butyl group).

According to the method disclosed in JP-A-11-171876, a 2-hydroxycarboxylic acid ester which can be produced from a 2-halocarboxylic acid ester is reacted with urea to produce a 5-alkyl-oxazolidin-2,4-dione.

The production method through a 2-halocarboxylic acid ester has a problem in that the process is prolonged due to the necessity of treating the waste liquid containing organic contents produced with the progress of reaction or purifying the intermediate.

An object of the present invention is to produce a 5-alkyl-oxazolidin-2,4-dione by an industrially advantageous method.

An object of the present invention is to supply a high-purity 5-alkyl-oxazolidin-2,4-dione.

DISCLOSURE OF INVENTION

As a result of extensive investigations to solve the above-described problems, the present inventors have found a process for producing a high-purity 5-alkyl-oxazolidin-2,4-dione represented by formula (2) by reacting a 2-hydroxycarboxylic acid amide represented by formula (1) with a carbonic acid ester in the presence of a metal alcoholate, thereby completing the reaction in one step, and then isolating the reaction product by a neutralization crystallization method. The present invention has been accomplished based on this finding.

The 2-hydroxycarboxylic acid amide is represented by the following formula (1), and is sometimes referred to as 2-hydroxyalkanoic acid amide or α-hydroxycarboxylic acid amide.

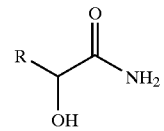

(1)

(wherein R represents an ethyl group, a propyl group or a butyl group).

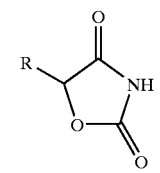

(2)

(wherein R represents an ethyl group, a propyl group or a butyl group).

More specifically, the present invention relates to the following matters.

[1] A process for producing a 5-alkyl-oxazolidin-2,4-dione represented by formula (2), comprising reacting a 2-hydroxycarboxylic acid amide represented by formula (1) with a carbonic acid ester in the presence of a metal alcoholate:

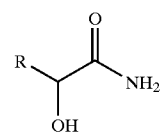

(1)

(wherein R represents an ethyl group, a propyl group or a butyl group).

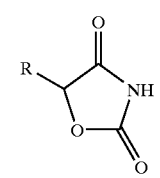

(2)

(wherein R represents an ethyl group, a propyl group or a butyl group).

[2] The process for producing a 5-alkyl-oxazolidin-2,4-dione as described in [1], wherein the used 2-hydroxycarboxylic acid amide has a water content of 5 mass % or less.

[3] The process for producing a 5-alkyl-oxazolidin-2,4-dione as described in [1] or [2], wherein a crystal of the 2-hydroxycarboxylic acid amide is used.

[4] The process for producing a 5-alkyl-oxazolidin-2,4-dione as described in any one of [1] to [3], wherein the used 2-hydroxycarboxylic acid amide has an acidic component content of 5 mass % or less in terms of sulfuric acid.

[5] The process for producing a 5-alkyl-oxazolidin-2,4-dione as described in any one of [1] to [4], wherein the metal alcoholate is a sodium alcoholate.

[6] The process for producing a 5-alkyl-oxazolidin-2,4-dione as described in [5], wherein the sodium alcoholate is sodium methylate and/or sodium ethylate.

[7] The process for producing a 5-alkyl-oxazolidin-2,4-dione as described in any one of [1] to [6], wherein the carbonic acid ester is at least one ester selected from the group consisting of dimethyl carbonate, diethyl carbonate, methyl chlorocarbonate and ethyl chlorocarbonate.

[8] The process for producing a 5-alkyl-oxazolidin-2,4-dione as described in any one of [1] to [7], wherein the equivalent ratio of the 2-hydroxycarboxylic acid amide, the carbonic acid ester and the metal alcoholate is 1:1.0 to 1.5:1.0 to 1.5.

[9] The process for producing a 5-alkyl-oxazolidin-2,4-dione as described in any one of [1] to [8], wherein the water content in the solution of starting materials other than the metal alcoholate is 3 mass % or less.

[10] A process for producing a 5-alkyl-oxazolidin-2,4-dione, comprising the step of isolating the 5-alkyl-oxazolidin-2,4-dione represented by formula (2) from the 5-alkyl-oxazolidin-2,4-dione metal salt represented by formula (3) obtained in the reaction solution resulting from the process described in any one of [1] to [9], the reaction solution is neutralized with a mineral acid to adjust the pH:

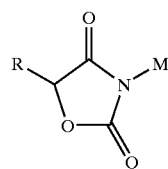

(3)

(wherein R represents an ethyl group, a propyl group or a butyl group, and M represents an alkali or alkaline earth (½ portion) metal).

[11] The process for producing a 5-alkyl-oxazolidin-2,4-dione as described in [10], wherein the neutralization with a mineral acid is performed in parts of twice or more to adjust the final hydrogen ion concentration of the solution to a pH of 5 or less.

[12] The process for producing a 5-alkyl-oxazolidin-2,4-dione as described in [11], wherein the reaction solution is adjusted to a pH of 6 to 10 by the neutralization with a mineral acid and after the adjustment of concentration, the final hydrogen ion concentration is adjusted to a pH of 5 or less by the neutralization with a mineral acid.

[13] The process for producing a 5-alkyl-oxazolidin-2,4-dione as described in [12], wherein the alcohol concentration is adjusted to 7 mass % or less by distilling off the alcohol.

[14] The process for producing a 5-alkyl-oxazolidin-2,4-dione as described in [12] or [13], wherein the concentration of 5-alkyl-oxazolidin-2,4-dione in the solution is adjusted to from 10 to 40 mass %.

[15] The process for producing a 5-alkyl-oxazolidin-2,4-dione as described in [10], wherein the reaction solution is adjusted to a pH of 9 or less by the neutralization with a mineral acid and after the adjustment of concentration, cooled.

[16] The process for producing a 5-alkyl-oxazolidin-2,4-dione as described in [15], wherein the alcohol concentration is adjusted to 7 mass % or less by distilling off the alcohol

[17] The production process for 5-alkyl-oxazolidin-2,4-dione as described in [15] or [16], wherein the concentration of 5-alkyl-oxazolidin-2,4-dione in the solution is adjusted to from 10 to 40 mass %.

[18] The process for producing a 5-alkyl-oxazolidin-2,4-dione as described in any one of [10] to [17], wherein after adjusting the pH by the neutralization with a mineral acid, the concentration of inorganic salts contained in the solution is adjusted to from 10 to 35 mass % in the solution.

[19] A process for producing a 5-alkyl-oxazolidin-2,4-dione, comprising dissolving a low-purity 5-alkyl-oxazolidin-2,4-dione in an aqueous alkali metal hydroxide solution and recrystallizing it by neutralization to obtain a high-purity 5-alkyl-oxazolidin-2,4-dione.

[20] The process for producing a 5-alkyl-oxazolidin-2,4-dione as described in [19], wherein the purity of the low-purity 5-alkyl-oxazolidin-2,4-dione is from 90.0 to less than 99.0 mass % and the purity of the high-purity 5-alkyl-oxazolidin-2,4-dione is 99.0 mass % or more.

[21] The process for producing a 5-alkyl-oxazolidin-2,4-dione as described in [19] or [20], wherein the alkyl group at the 5-position of 5-alkyl-oxazolidin-2,4-dione is an alkyl group having from 1 to 4 carbon atoms.

[22] The process for producing a 5-alkyl-oxazolidin-2,4-dione as described in [21] above, wherein the alkyl group at the 5-position is an ethyl group, a propyl group or a butyl group.

[23] The process for producing a 5-alkyl-oxazolidin-2,4-dione as described in any one of [1] to [18], which further comprises a step of dissolving a 5-alkyl-oxazolidin-2,4-dione in an aqueous alkali metal hydroxide solution and recrystallizing it by neutralization to obtain a high-purity 5-alkyl-oxazolidin-2,4-dione.

[24] The process for producing a 5-alkyl-oxazolidin-2,4-dione as described in any one of [1] to [18], wherein the organic solvent which can be recovered from the reaction solution is reused.

[25] The process for producing a 5-alkyl-oxazolidin-2,4-dione as described in any one of [1] to [18], [23] and [24], wherein the 2-hydroxycarboxylic acid amide is 2-hydroxyhexanoic acid amide and the 5-alkyl-oxazolidin-2,4-dione is 5-butyl-oxazolidin-2,4-dione.

[26] The process for producing a 5-alkyl-oxazolidin-2,4-dione as described in any one of [19] to [22], wherein the 5-alkyl-oxazolidin-2,4-dione is 5-butyl-oxazolidin-2,4-dione.

[27] A 5-alkyl-oxazolidin-2,4-dione having a purity of 99.0% or more.

[28] The 5-alkyl-oxazolidin-2,4-dione as described in [27], wherein the content of inorganic salts is 0.2% or less.

[29] A 5-butyl-oxazolidin-2,4-dione having a purity of 99.0% or more.

[30] The 5-butyl-oxazolidin-2,4-dione as described in [29], wherein the content of inorganic salts is 0.2% or less.

MODE FOR CARRYING OUT THE INVENTION

An objective 5-alkyl-oxazolidin-2,4-dione of the present invention is represented by formula (2) and in particular, 5-butyl-oxazolidin-2,4-dione is preferred as a raw material of photographic chemicals.

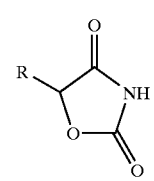

(2)

(wherein R represents an ethyl group, a propyl group or a butyl group).

The 2-hydroxycarboxylic acid amide represented by formula (1) as a starting material of the production can be produced by the amidation of a corresponding ester, the introduction of a hydroxy group into a straight chain amide compound or the hydration of a nitrile form.

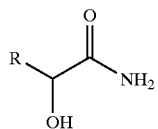
(1)

(wherein R represents an ethyl group, a propyl group or a butyl group).

Examples of the preferred processes for producing 2-hydroxycarboxylic acid amide are as follows.

(1) A process comprising reacting 2-hydroxynitrile represented by formula (A) with sulfuric acid under such condition that the water content in the reaction system is 20 mass % or less at a temperature of 80° C. or less;

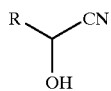
(A)

(wherein R has the same meanings as mentioned above)
to thereby produce 2-hydroxycarboxylic acid amide represented by above formula (1).

(2) The process described in (1), wherein the amount of sulfuric acid is 1.5 to 5 mol per 1 mol of 2-hydroxynitrile.

(3) The process described in (1) or (2), wherein the reaction of 2-hydroxynitrile and sulfuric acid is conducted in the reaction system comprising inert organic solvent having boiling point of 30 to 70° C.

Examples of the inert organic solvent include hydrocarbons such as pentane, hexane and heptane, halogenated hydrocarbons such as dichloromethane, chloroform, and dialkylethers such as diethylether.

One or more of the inert solvents may be used in the reaction.

(4) The process described in (1) or (2), wherein the reaction of 2-hydroxynitrile and sulfuric acid is conducted in the reaction system containing water of 5 mol or less per 1 mol of 2-hydroxynitrile.

(5) The process described in any one of (1) to (4), wherein to the reaction mixture comprising 2-hydroxylsulfonyloxy carboxylic acid amide represented by formula (B) which is an intermediate of the reaction of 2-hydroxynitrile and sulfuric acid, is added an alcohol at temperature of 50° C. or less to thereby performing alcoholysis of the intermediate.

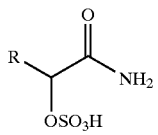
(B)

(wherein R has the same meanings as mentioned above)
(6) The process described in (5), wherein the amount of alcohol is 1 to 10 mol per 1 mol of 2-hydroxylsulfonyloxy carboxylic acid amide.

(7) The process described in (5) or (6), wherein the alcoholysis is conducted at pH of 7 or less.

(8) The process described in any one of (5) to (7), wherein the alcohol is methyl alcohol.

(9) The process described in any one of (1) to (4), wherein to the reaction mixture comprising 2-hydroxylsulfonyloxy carboxylic acid amide represented by formula (B) which is an intermediate of the reaction of 2-hydroxynitrile and sulfuric acid, is added water at temperature of 70° C. or less to thereby performing hydrolysis of the intermediate.

(10) The process described in (9), wherein the hydrolysis is conducted at pH of 3 or less.

(11) The process described in (9) or (10) wherein the amount of water is 1 to 50 mol per 1 mol of 2-hydroxylsulfonyloxy carboxylic acid amide.

(12) A process comprising adding alcohol or water to the reaction mixture comprising 2-hydroxylsulfonyloxy carboxylic acid amide represented by formula (B) which is an intermediate of the reaction of 2-hydroxynitrile and sulfuric acid, to thereby converting the 2-hydroxylsulfonyloxy carboxylic acid amide to 2-hydroxycarboxylic acid amide, neutralizing the reaction mixture to pH of 5 to 8, and isolating the 2-hydroxycarboxylic acid amide.

(13) The process described in (12), wherein the neutralization of the reaction mixture to pH of 5 to 8 is conducted at temperature of 60° C. or less.

(14) The process described in any one of (1) to (12), wherein the 2-hydroxynitrile is 2-hydroxyhexanonitrile, and 2-hydroxycarboxylic acid amide is 2-hydroxyhexanoic acid amide.

(15) The process described in (14), wherein the amount of sulfuric acid is 1.5 to 5 mol per 1 mol of 2-hydroxyhexanonitrile.

(16) The process described in (14) or (15), wherein the reaction of 2-hydroxyhexanonitrile and sulfuric acid is conducted in the reaction system comprising inert organic solvent having boiling point of 30 to 70° C.

(17) The process described in any one of (14) to (16), wherein to the reaction mixture comprising 2-hydroxylsulfonyloxy hexanoicic acid amide which is an intermediate of the reaction of 2-hydroxyhexanonitrile and sulfuric acid, is added an alcohol at temperature of 50° C. or less to thereby performing alcoholysis of the intermediate.

(18) The process described in (17), wherein the alcoholysis is conducted at pH of 7 or less.

(19) The process described in (17) or (18), wherein the amount of alcohol is 1 to 10 mol per 1 mol of 2-hydroxylsulfonyloxy hexanoic acid amide.

(20) The process described in any one of (14) to (16), wherein to the reaction mixture comprising 2-hydroxylsulfonyloxy hexanoic acid amide which is an intermediate of the reaction of 2-hydroxyhexanonitrile and sulfuric acid, is added water at temperature of 70° C. or less to thereby performing hydrolysis of the intermediate

(21) The process described in (20), wherein the amount of water is 1 to 50 mol per 1 mol of 2-hydroxylsulfonyloxy hexanoic acid amide.

(22) The process described in (20) or (21), wherein the hydrolysis is conducted at pH of 3 or less.

2-Hydroxynitrile represented by formula (A) can be produced by reacting a corresponding aldehyde and cyanic compounds.

The 2-hydroxycarboxylic acid amide preferably has a quality suitable for use in the production of a 5-alkyl-oxazolidin-2,4-dione. Specifically, the water content in the 2-hydroxycarboxylic acid amide is more preferably 5 mass % or less based on the mass of crystal. Even if the water content is in excess of 5 mass %, the 2-hydroxycarboxylic acid amide can be used, however, the yield may decrease due to the water content or the yield by volume may decrease due to the decomposition of starting materials or product. In this case, the adverse influence of water can be suppressed by increasing the molar equivalent number of metal alcoholate or carbonic acid ester or by adding a dehydrating agent, however, this method is not suitable in industry.

The 2-hydroxycarboxylic acid amide having a water content of 5 mass % or less can be produced by subjecting the 2-hydroxycarboxylic acid amide produced by the above-described method to washing with an alcohol or drying using a drier such as conical drier.

The starting material 2-hydroxycarboxylic acid amide preferably has an acidic component content of, in terms of sulfuric acid, 5 mass % or less, more preferably 1 mass % or less. Such a 2-hydroxycarboxylic acid amide can be produced by the washing with water such as rinse.

After the 2-hydroxycarboxylic acid amide and a carbonic acid ester are admixed, a metal alcoholate is added thereto, whereby a 5-alkyl-oxazolidin-2,4-dione can be obtained in the reaction finish solution as a 5-alkyl-oxazolidin-2,4-dione metal salt represented by formula (3):

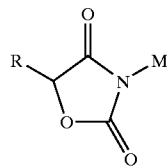

(3)

(wherein R represents an ethyl group, a propyl group or a butyl group, and M represents an alkali or alkaline earth (½ portion) metal).

If desired, an organic solvent not participating in the reaction may be added so as to improve the fluidity and solubility of the reaction solution. In this case, an alcohol is preferably added.

In the mixed solution of 2-hydroxycarboxylic acid amide, alcohol and carbonic acid ester, the water content is preferably 3 mass % or less. This mixed solution may be a solution or a slurry of 2-hydroxycarboxylic acid amide. After adding the metal alcoholate, the reaction solution is heated to a temperature of 50 to 100° C., whereby the reaction can be completed. Usually, the reaction time is about 3 hours and the completion of reaction can be judged by analyzing the concentration of 2-hydroxycarboxylic acid amide or 5-alkyl-oxazolidin-2,4-dione in the solution.

Examples of the carbonic acid ester which can be used in the reaction include a carbonylating agent such as dimethyl carbonate, diethyl carbonate, methyl chlorocarbonate, ethyl chlorocarbonate, carbonyl diimidazole and urea. These carbonic acid esters can be used individually or in combination of two or more thereof. The carbonic acid ester is suitably used in an amount of 1.0 to 1.5 molar equivalent, preferably from 1.0 to 1.3 molar equivalent, based on the molar number of 2-hydroxycarboxylic acid amide.

The metal alcoholate is preferably a methylate or ethylate of an alkali or alkaline earth metal such as sodium, potassium and magnesium, more preferably sodium methylate or sodium ethylate. The metal alcoholate may be used in the solid form, however, preferably used in the solution form in view of handling. The metal alcoholate is suitably used in an amount of 1.0 to 1.5 molar equivalent, preferably from 1.0 to 1.3 molar equivalent, based on the molar number of 2-hydroxycarboxylic acid amide. In the production of a 5-alkyl-oxazolidin-2,4-dione metal salt from a 2-hydroxycarboxylic acid amide, a carbonic acid ester and a metal alcoholate, the order of adding the starting materials is not particularly limited and any starting material may be added first. Also, these starting materials may be added batchwise or in parts. Furthermore, if the conversion of 2-hydroxycarboxylic acid amide is not sufficiently high, either one or both of the carbonic acid ester and the metal alcoholate may be additionally added in an appropriate amount.

From the reaction solution where the completion of reaction is confirmed by the high-performance liquid chromatography (HPLC) or the like, the solvent is removed by distillation under reduced pressure. About 80% or more of the alcohol contained in the reaction solution is removed by distillation. The alcohol removed by distillation at this time can be reused in the reaction. After the completion of removal by distillation, water is added and then, the pH is adjusted with a mineral acid to 6 to 10. At this time, water may be added such that the concentration of 5-alkyl-oxazolidin-2,4-dione metal salt in the solution becomes from 10 to 30 mass %. The mineral acid used for the neutralization may be any of a hydrochloric acid, a nitric acid and a sulfuric acid. With respect to the concentration of mineral acid, either dilute mineral acid or concentrated mineral acid can be used.

When the pH is adjusted to 6 or less, a crystal of 5-alkyl-oxazolidin-2,4-dione sometimes precipitates and this crystal may be recovered by a centrifugal separator or the like, however, the recovery decreases due to the alcohol remaining in the solution. In some cases, the 5-alkyl-oxazolidin-2,4-dione becomes oily. This oily substance contains impurities and the content of 5-alkyl-oxazolidin-2,4-dione is low in many cases.

After the adjustment of pH, the reaction solution is distilled off under reduced pressure to lower the alcohol concentration in the solution to 7 mass % or less. To this solution, water is added to adjust the concentration such that the concentration of 5-alkyl-oxazolidin-2,4-dione metal salt in the solution becomes from 10 to 40 mass %. The solution after the adjustment of concentration is used for crystallization and this solution is called a mother liquor for crystallization of 5-alkyl-oxazolidin-2,4-dione.

To the mother liquor for crystallization, a mineral acid is gradually added dropwise while stirring to lower the pH, in particular, to a pH of 5 or less, whereby a 5-alkyl-oxazolidin-2,4-dione can be obtained as a pale yellow or white crystal. The temperature at the crystallization is preferably 70° C. or less. If the crystallization temperature exceeds this range, the crystal precipitated is dissolved out. When crystallization is difficult to occur, the crystallization may be started by adding a crystal of 5-alkyl-oxazolidin-2,4-dione as a seed crystal.

In the case where the pH of the mother liquor for crystallization is 9 or less, preferably from 6 to 9, the crystallization may also be effectively performed by cooling the mother liquor for crystallization to 20° C. or less in place of lowering the pH by adding a mineral acid.

The crystal obtained can be recovered by an apparatus such as centrifugal separator. From the standpoint of reducing impurities, the crystal is preferably washed with an organic solvent or water. When the recovered crystal is dried by a conical drier or the like, a 5-alkyl-oxazolidin-2,4-dione crystal having a purity of 99.0 mass % or more can be obtained. In the crystal obtained by this method, the inorganic salt content is 1.0 mass % or less.

The 5-alkyl-oxazolidin-2,4-dione turned into an oily form by neutralization after the reaction or the 5-alkyl-oxazolidin-2,4-dione having a purity of less than 99.0 mass %, particularly from 90.0 to less than 99.0 mass %, can be re-purified by dissolving it in an aqueous alkali metal hydroxide solution and then, neutralizing the solution with a mineral acid, whereby a crystal having a dry content of 99.0 mass % or more can be obtained.

EXAMPLES

The present invention is described in greater detail below by referring to Examples, however, the present invention is not limited to these Examples.

In Examples, high-performance liquid chromatography (hereinafter referred to as "HPLC analysis") was performed and the analysis conditions are as follows.

Column: Shodex DM-614, produced by Showa Denko K.K. (length: 15 cm, inside diameter: 0.6 cm)

Column temperature condition: 40° C.

Eluent: aqueous 0.1% $H_3PO_4$ solution

Flow rate: 1.0 ml/min

Detection: RI, UV (detection wavelength: 210 nm)

The acid content in the 2-hydroxycarboxylic acid amide was measured by the following method.

Analysis: After 2-hydroxycarboxylic acid amide was dissolved in an aqueous 50 mass % methyl alcohol solution, the solution was titrated by an automatic titrator using an aqueous 0.1 mol/L-NaOH solution. The acid content was calculated by the following formula:

Acid content, mass % (in terms of sulfuric acid)=(titer (ml)×0.1(mol/L)×factor×4.904)/mass of sample (g)

Factor: NaOH concentration correction factor

Reference Example

Preparation of 2-hydroxycarboxylic Acid Amide

A stirrer, a thermometer and a dropping funnel were set to a 1,000-mL four-necked flask and to a reaction apparatus, 95% sulfuric acid (450 g, 4.4 mol) was added and cooled so that the liquid temperature was lower than 30° C. To the cooled sulfuric acid with stirring, was added α-n-butyl-α-hydroxyacetonitrile prepared from n-butyl aldehyde and hydrocyanic acid (1.5 mol, content 87 to 94%, further containing unreacted hydrocyanic acid, starting material n-butyl aldehyde and water) with the use of dropping funnel. The addition was conducted in such a way that the reaction solution was kept at a temperature of lower than 40° C. After the dropwise addition, the reaction solution was aged at 40° C. for 0.5 hr. The pH of the reaction solution was less than 1. A part of the reaction solution was sampled and analyzed by HPLC. In result, the ratio of conversion of the starting materials was 100% and the corresponding 2-hydroxyhexanoic acid amide and 2-hydroxysulfonyl oxy hexanoic acid amide were produced.

After the addition reaction, methyl alcohol or water (5.9 mol) was added dropwise with the dropping funnel to the reaction solution for about 2 hr so that the reaction solution was kept at a temperature of lower than 40° C. After completion of the dropwise addition of methyl alcohol or water, a part of the reaction solution was sampled and the component thereof was analyzed by HPLC. In result, the yield with addition of methyl alcohol was 96% and the yield with addition of water was 90%.

A stirrer, a thermometer, a dropping funnel and a pH controller with pH meter electrodes were set to a 5,000-mL four-necked flask and then thereto, 1440 g of water was added. The reaction solution prepared with addition of water in the above (pH: less than 1) was added gradually to the present reaction apparatus so that the solution was kept at 40° C., to deposit crystals. According to the feeding amount of the reaction solution, the adding amount of a 48% sodium hydroxide aqueous solution was regulated by controlling the flow rate with the pH controller so that the hydrogen ion concentration of the reaction solution was kept to pH 6 to 8.

The solution was cooled to 25° C. and crystals were recovered by centrifugation. The resultant crystals had a 2-hydroxyhexanoic acid amide content of 83%, a water content of 15%, a 2-hydroxyhexanoic acid content of 1% and a sodium sulfate content of 1%.

The crude crystal of 2-hydroxy hexanoic acid amide was taken out and put in a conical dryer equipped with a jacket and dried with stirring under reduced pressure of 25 mmHg until the crystal temperature reached to 65° C., while hot water was passed through the jacket. After the drying, the crystal of 2-hydroxyhexanoic acid amide was cooled and taken out. As a result of the moisture analysis thereof, the water content was 2.5 wt %.

Example 1

A condenser tube, a stirrer, a thermometer and a dropping funnel were set to a 2,000-mL four-necked flask and then thereto, 2-hydroxyhexanoic acid amide (267 g, 2.04 mol, water content: 0.7 mass %, acidic component: 0.3 mass % (in terms of sulfuric acid)), 267 g of methyl alcohol and dimethyl carbonate (239 g, 2.65 mol) were added. Furthermore, 30 mass % sodium methylate (477 g, 2.65 mol) was added at a rate of 10 mol/hr through the dropping funnel. After the completion of addition, the solution was stirred for 2 hours while keeping the reaction temperature at 60 to 70° C. After 2 hours, a part of the reaction solution was sampled and the components were analyzed by HPLC, as a result, the starting material 2-hydroxyhexanoic acid amide was not recognized and the concentration of 5-alkyl-oxazolidin-2,4-dione sodium salt as the objective product was 28.0 mass % in the solution. From this analysis value, the yield in terms of 5-alkyl-oxazolidin-2,4-dione was 96%.

After the completion of reaction, the solution was distilled off under reduced pressure to remove 85% of methyl alcohol in the reaction solution. To the solution after distilling off, 1,158 g of purified water was added to adjust the concentration of 5-alkyl-oxazolidin-2,4-dione metal salt in the solution to 20 mass %.

While stirring this solution, a concentrated sulfuric acid was added dropwise and thereby, the pH of the solution was adjusted to 8.0. After the adjustment of pH, the solution was distilled off under reduced pressure until the methyl alcohol concentration in the solution was lowered to 1 mass % or less. After the distilling off, purified water was added to the solution and thereby, the concentration of 5-butyl-oxazolidin-2,4-dione metal salt in the solution was adjusted to 20 mass %. This solution adjusted in the concentration was used as the mother liquor for crystallization.

To the mother liquor for crystallization, a concentrated sulfuric acid was gradually added at about 40° C., whereupon a crystal of 5-butyl-oxazolidin-2,4-dione was precipitated. At the completion of crystallization, the hydrogen ion concentration of the crystallization solution was a pH of 3.

The crystal precipitated was recovered by a centrifugal separator to obtain 293.5 g of 5-butyl-oxazolidin-2,4-dione crystal. This crystal was analyzed, as a result, the purity of 5-butyl-oxazolidin-2,4-dione was 99.5 mass % and the inorganic salt content was 0.1 mass %.

Example 2

2-Hydroxyhexanoic acid amide (267 g, 2.04 mol, water content: 1.0 mass %, acidic component: 0.6 mass % (in terms of sulfuric acid)), 267 g of methyl alcohol and dimethyl carbonate (239 g, 2.65 mol) were added. Using 30 mass % sodium methylate (477 g, 2.65 mol), the reaction was performed in the same manner as in Example 1. After the completion of reaction, the solution was distilled off under reduced pressure to remove methyl alcohol and thereby, 85% of methyl alcohol in the reaction solution was removed by distillation. To the solution after distilling off, 1,158 g of purified water was added and thereby, the concentration of 5-butyl-oxazolidin-2,4-dione metal salt in the solution was adjusted to 20 mass %. While stirring this solution, a concentrated sulfuric acid was added dropwise to adjust the solution to a pH of 3, as a result, an oil-dispersed state was presented.

The oil dispersion solution was cooled and the crystal obtained was separated by centrifugation. After drying the yellow crystal obtained, the purity of 5-butyl-oxazolidin-2,4-dione in the crystal was measured and found to be 95.2 mass %.

Example 3

2-Hydroxyhexanoic acid amide (267 g, 2.04 mol, water content: 0.7 mass %, acidic component: 0.3 mass % (in terms of sulfuric acid)), 267 g of methyl alcohol and dimethyl carbonate (165 g, 1.84 mol) were added. The reaction was performed according to Example 1 except for using 30 mass % of sodium methylate (331 g, 1.84 mol).

A part of the reaction solution was sampled and the components of the reaction solution were analyzed by HPLC, as a result, the concentration of the starting material 2-hydroxyhexanoic acid amide was 3.6 mass % in the solution and the concentration of 5-butyl-oxazolidin-2,4-dione as the objective product was 30.4 mass % in the solution. From these analysis values, the conversion of 2-hydroxyhexanoic acid amide was 86% and the yield in terms of 5-butyl-oxazolidin-2,4-dione was 85.5%.

To this solution, dimethyl carbonate (74 g, 0.82 mol) and 30% sodium methylate (147 g, 0.82 mol) were again added and reacted at from 60 to 70° C. for 2 hours. Thereafter, a part of the reaction solution was sampled and the components of the reaction solution were analyzed by HPLC, as a result, the concentration of 2-hydroxyhexanoic acid amide was 0 mass % in the solution and the concentration of 5-butyl-oxazolidin-2,4-dione sodium salt as the objective product was 27.5% in the solution. From these analysis values, the conversion of 2-hydroxyhexanoic acid amide was 100% and the yield in terms of 5-butyl-oxazolidin-2,4-dione was 94.1%.

Example 4

2-Hydroxyhexanoic acid amide (267 g, 2.04 mol, acidic component: 1.2 mass % (in terms of sulfuric acid)) having a water content of 10 mass % in the crystal, 267 g of methyl alcohol and dimethyl carbonate (239 g, 2.65 mol) were added. The reaction was performed according to Example 1 except for using 30 mass % of sodium methylate (477 g, 2.65 mol).

A part of the reaction solution was sampled and the components of the reaction solution were analyzed by HPLC, as a result, the concentration of the starting material 2-hydroxyhexanoic acid amide was 1.6 mass % in the solution, the concentration of 5-butyl-oxazolidin-2,4-dione sodium salt as the objective product was 24.0 mass % in the solution and the concentration of 2-hydroxyhexanoic acid was 2.3 mass % in the solution. From these analysis values, the conversion of 2-hydroxyhexanoic acid amide was 92.6% and the yield in terms of 5-butyl-oxazolidin-2,4-dione was 82.1%.

Example 5

2-Hydroxyhexanoic acid amide (267 g, 2.04 mol, water content: 0.9 mass %) having an acidic component content of 5.5 mass % in the crystal, 267 g of methyl alcohol and dimethyl carbonate (239 g, 2.65 mol) were added. The reaction was performed according to Example 1 except for using 30 mass % of sodium methylate (477 g, 2.65 mol).

A part of the reaction solution was sampled and the components of the reaction solution were analyzed by HPLC, as a result, the concentration of the starting material 2-hydroxyhexanoic acid amide was 1.3 mass % in the solution and the concentration of 5-butyl-oxazolidin-2,4-dione sodium salt as the objective product was 25.9 mass % in the solution. From these analysis values, the conversion of 2-hydroxyhexanoic acid amide was 93.8% and the yield in terms of 5-butyl-oxazolidin-2,4-dione was 88.7%.

Example 6

The reaction was performed in the same manner as in Example 1 and thereafter, the reaction solution was adjusted to a pH of 8 and distilled off to a methanol concentration of about 1 mass %. The obtained mother liquor for crystallization (28.5° C.) was subjected to the adjustment of concentration with purified water and then gradually cooled to 19° C. or less. The colorless crystal produced upon cooling was recovered by centrifugal separation to obtain 284.3 g of 5-butyl-oxazolidin-2,4-dione crystal.

This crystal was analyzed, as a result, the purity of 5-butyl-oxazolidin-2,4-dione was 99.4 mass % and the inorganic salt content was 0.05 mass %.

Example 7

To a 1,000-mL four-necked flask equipped with a stirring blade, a thermometer and a dropping funnel, 165 g of a crystal (purity of 5-butyl-oxazolidin-2,4-dione in the crystal: 95.2 mass %) and 700 g of purified water were added. Thereto, 48% sodium hydroxide was added and the mixture was dissolved while stirring. At this time, the hydrogen ion concentration in the solution was a pH of 9.

Using this solution as a mother liquor for crystallization, the neutralization crystallization with sulfuric acid was performed in the same manner as in Example 1. The purity after drying of the crystal obtained was determined by HPLC and found to be 99.7 mass %. The recovery based on the re-dissolved 5-butyl-oxazolidin-2,4-dione was 96.5%.

EFFECTS OF THE INVENTION

According to the present invention, a high-purity 5-alkyl-oxazolidin-2,4-dione can be synthesized by a short process starting from a 2-hydroxycarboxylic acid amide. This product can be used over a wide range as a raw material of photographic chemicals, an industrial raw material or an intermediate of medical or agrochemical preparations.

What is claimed is:

1. A process for producing a 5-alkyl-oxazolidin-2,4-dione represented by formula (2), comprising reacting a 2-hydroxycarboxylic acid amide represented by formula (1) with a carbonic acid ester in the presence of a metal alcoholate:

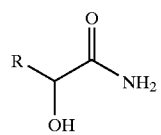

(wherein R represents an ethyl group, a propyl group or a butyl group);

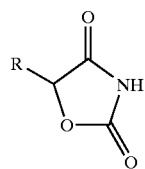

(wherein R represents an ethyl group, a propyl group or a butyl group), wherein the 2-hydroxycarboxylic acid amide has a water content of 5 mass % or less.

2. The process for producing a 5-alkyl-oxazolidin-2,4-dione as claimed in claim 1, wherein a crystal of the 2-hydroxycarboxylic acid amide is used.

3. The process for producing a 5-alkyl-oxazolidin-2,4-dione as claimed in claim 1, wherein the 2-hydroxycarboxylic acid amide has an acidic component content of 5 mass % or less in terms of sulfuric acid.

4. The process for producing a 5-alkyl-oxazolidin-2,4-dione as claimed in claim 1, wherein the metal alcoholate is a sodium alcoholate.

5. The process for producing a 5-alkyl-oxazolidin-2,4-dione as claimed in claim 4, wherein the sodium alcoholate is sodium methylate and/or sodium ethylate.

6. The process for producing a 5-alkyl-oxazolidin-2,4-dione as claimed in claim 1, wherein the carbonic acid ester is at least one ester selected from the group consisting of dimethyl carbonate, diethyl carbonate, methyl chlorocarbonate and ethyl chlorocarbonate.

7. The process for producing a 5-alkyl-oxazolidin-2,4-dione as claimed in claim 1, wherein the equivalent ratio of the 2-hydroxycarboxylic acid amide, the carbonic acid ester and the metal alcoholate is 1:1.0 to 1.5:1.0 to 1.5.

8. The process for producing a 5-alkyl-oxazolidin-2,4-dione as claimed in claim 1, wherein the water content in the solution of starting materials other than the metal alcoholate is 3 mass % or less.

9. A process for producing a 5-alkyl-oxazolidin-2,4-dione, comprising the step of isolating the 5-alkyl-oxazolidin-2,4-dione represented by formula (2) from the 5-alkyl-oxazolidin-2,4-dione metal salt represented by formula (3) obtained in the reaction solution resulting from the process claimed in claim 1, wherein the reaction solution is neutralized with a mineral acid to adjust the pH:

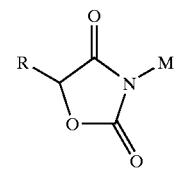

(wherein R represents an ethyl group, a propyl group or a butyl group, and M represents an alkali or alkaline earth (½ portion) metal).

10. The process for producing a 5-alkyl-oxazolidin-2,4-dione as claimed in claim 9, wherein the neutralization with a mineral acid is performed in parts of twice or more to adjust the final hydrogen ion concentration of the solution to a pH of 5 or less.

11. The process for producing a 5-alkyl-oxazolidin-2,4-dione as claimed in claim 10, wherein the reaction solution is adjusted to a pH of 6 to 10 by the neutralization with a mineral acid and after the adjustment of concentration, the final hydrogen ion concentration is adjusted to a pH of 5 or less by the neutralization with a mineral acid.

12. The process for producing a 5-alkyl-oxazolidin-2,4-dione as claimed in claim 11, wherein the alcohol concentration is adjusted to 7 mass % or less by distilling off the alcohol.

13. The process for producing a 5-alkyl-oxazolidin-2,4-dione as claimed in claim 11, wherein the concentration of 5-alkyl-oxazolidin-2,4-dione in the solution is adjusted to from 10 to 40 mass %.

14. The process for producing a 5-alkyl-oxazolidin-2,4-dione as claimed in claim 9, wherein the reaction solution is adjusted to a pH of 9 or less by the neutralization with a mineral acid and after the adjustment of concentration, cooled.

15. The process for producing a 5-alkyl-oxazolidin-2,4-dione as claimed in claim 14, wherein the alcohol concentration is adjusted to 7 mass % or less by distilling off the alcohol.

16. The production process for 5-alkyl-oxazolidin-2,4-dione as claimed in claim 14, wherein the concentration of 5-alkyl-oxazolidin-2,4-dione in the solution is adjusted to from 10 to 40 mass %.

17. The process for producing a 5-alkyl-oxazolidin-2,4-dione as claimed in claim 9, wherein after adjusting the pH by the neutralization with a mineral acid, the concentration of inorganic salts contained in the solution is adjusted to from 10 to 35 mass % in the solution.

18. The process for producing a 5-alkyl-oxazolidin-2,4-dione as claimed in claim 1, which further comprises a step of dissolving a 5-alkyl-oxazolidin-2,4-dione in an aqueous alkali metal hydroxide solution and recrystallizing it by neutralization to obtain a high-purity 5-alkyl-oxazolidin-2,4-dione.

19. The process for producing a 5-alkyl-oxazolidin-2,4-dione as claimed in claim 1, wherein an organic solvent which can be recovered from a reaction solution is reused.

20. The process for producing a 5-alkyl-oxazolidin-2,4-dione as claimed in claim 1, wherein the 2-hydroxycarboxylic acid amide is 2-hydroxyhexanoic acid amide and the 5-alkyl-oxazolidin-2,4-dione is 5-butyl-oxazolidin-2,4-dione.

21. A process for producing a 5-alkyl-oxazolidin-2,4-dione represented by formula (2), comprising reacting a 2-hydroxycarboxylic acid amide represented by formula (1)

with a carbonic acid ester in the presence of a metal alcoholate:

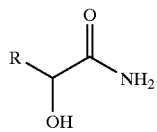
(1)

(wherein R represents an ethyl group, a propyl group or a butyl group);

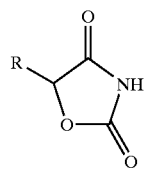
(2)

(wherein R represents an ethyl group, a propyl group or a butyl group), wherein the 2-hydroxycarboxylic acid amide has an acidic component content of 5 mass % or less in terms of sulfuric acid.

22. A process for producing a 5-alkyl-oxazolidin-2,4-dione represented by formula (2), comprising reacting a 2-hydroxycarboxylic acid amide represented by formula (1) with a carbonic acid ester in the presence of a metal alcoholate:

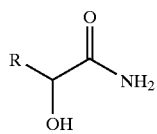
(1)

(wherein R represents an ethyl group, a propyl group or a butyl group);

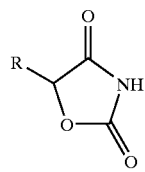
(2)

(wherein R represents an ethyl group, a propyl group or a butyl group), wherein the water content in the solution of starting materials other than the metal alcoholate is 3 mass % or less.

23. A process for producing a 5-alkyl-oxazolidin-2,4-dione, comprising reacting a 2-hydroxycarboxylic acid amide represented by formula (1) with a carbonic acid ester in the presence of a metal alcoholate:

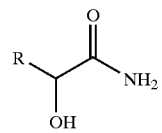
(1)

(wherein R represents an ethyl group, a propyl group or a butyl group) to obtain a reaction solution containing a 5-alkyl-oxazolidin-2,4-dione metal salt represented by formula (3):

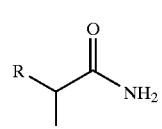
(1)

(wherein R represents an ethyl group, a propyl group or a butyl group, and M represents an alkali or alkaline earth (½ portion) metal); and isolating the 5-alkyl-oxazolidin-2,4-dione represented by formula (2) from the 5-alkyl-oxazolidin-2,4-dione metal salt:

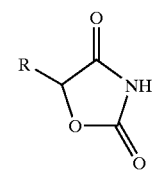
(2)

(wherein R represents an ethyl group, a propyl group or a butyl group), wherein the reaction solution is neutralized with a mineral acid to adjust the pH, and wherein the neutralization with a mineral acid is performed in parts of twice or more to adjust the final hydrogen ion concentration of the solution to a pH of 5 or less.

24. The process for producing a 5-alkyl-oxazolidin-2,4-dione as claimed in claim 23, wherein the reaction solution is adjusted to a pH of 6 to 10 by the neutralization with a mineral acid and after the adjustment of concentration, the final hydrogen ion concentration is adjusted to a pH of 5 or less by the neutralization with a mineral acid.

25. The process for producing a 5-alkyl-oxazolidin-2,4-dione as claimed in claim 24, wherein the alcohol concentration is adjusted to 7 mass % or less by distilling off the alcohol.

26. The process for producing a 5-alkyl-oxazolidin-2,4-dione as claimed in claim 24, wherein the concentration of 5-alkyl-oxazolidin-2,4-dione in the solution is adjusted to from 10 to 40 mass %.

27. A process for producing a high-purity 5-alkyl-oxazolidin-2,4-dione represented by formula (2), comprising reacting a 2-hydroxycarboxylic acid amide represented by formula (1) with a carbonic acid ester in the presence of a metal alcoholate:

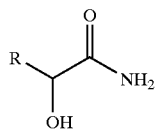

(1)

(wherein R represents an ethyl group, a propyl group or a butyl group);

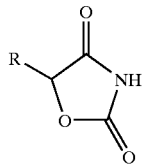

(2)

(wherein R represents an ethyl group, a propyl group or a butyl group), and dissolving a 5-alkyl-oxazolidin-2,4-dione in an aqueous alkali metal hydroxide solution and recrystallizing it by neutralization to obtain the high-purity 5-alkyl-oxazolidin-2,4-dione.

28. A process for producing a 5-alkyl-oxazolidin-2,4-dione represented by formula (2), comprising reacting a 2-hydroxycarboxylic acid amide represented by formula (1) with a carbonic acid ester in the presence of a metal alcoholate:

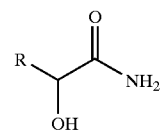

(1)

(wherein R represents an ethyl group, a propyl group or a butyl group);

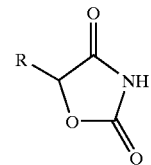

(2)

(wherein R represents an ethyl group, a propyl group or a butyl group), wherein an organic solvent which can be recovered from a reaction solution is reused.

* * * * *